United States Patent [19]
Rollins et al.

[11] Patent Number: 5,423,788
[45] Date of Patent: Jun. 13, 1995

[54] DISPOSABLE FEMININE GUARD

[75] Inventors: Neal A. Rollins, Menasha; Thomas P. Jorgenson, Neenah; Gregory J. Hess, Fremont; Alan F. Schleinz, Appleton, all of Wis.

[73] Assignee: Kimberly-Clark Corporation, Neenah, Wis.

[21] Appl. No.: 11,082

[22] Filed: Jan. 29, 1993

Related U.S. Application Data

[63] Continuation of Ser. No. 598,272, Oct. 16, 1990, abandoned.

[51] Int. Cl.$^6$ ............................................. A61F 13/15
[52] U.S. Cl. ................................. 604/385.1; 604/378; 604/368
[58] Field of Search ............... 604/358, 368, 378, 379, 604/385.1

[56] References Cited

U.S. PATENT DOCUMENTS

| | | | |
|---|---|---|---|
| Re. 32,649 | 4/1988 | Brandt et al. | 604/368 |
| 924,337 | 6/1909 | Frommann . | |
| 2,104,423 | 1/1938 | Hughes | 128/290 |
| 2,649,859 | 8/1953 | Hermanson et al. | 128/287 |
| 2,747,575 | 5/1956 | Mercer | 604/385.1 |
| 2,896,626 | 7/1959 | Voigtman | 128/287 |
| 3,106,207 | 10/1963 | Dudley | 128/290 |
| 3,371,667 | 3/1968 | Morse | 128/290 |
| 3,520,303 | 7/1970 | Endres | 128/287 |
| 3,570,491 | 3/1971 | Sneider | 128/290 |
| 3,587,579 | 6/1971 | Sabee | 128/287 |
| 3,670,731 | 6/1972 | Harmon | 128/284 |
| 3,672,371 | 6/1972 | Roeder | 128/290 |
| 3,732,867 | 5/1973 | Money | 604/379 |
| 3,805,790 | 4/1974 | Kaczmarzyk et al. | 128/290 R |
| 3,888,255 | 6/1975 | Shah et al. | 128/290 R |
| 3,900,031 | 8/1975 | Endres et al. | 128/287 |
| 3,978,861 | 9/1976 | Schaar | 128/287 |
| 3,993,074 | 11/1976 | Murray et al. | 128/286 |
| 4,102,340 | 7/1978 | Mesek et al. | 128/287 |
| 4,119,450 | 10/1978 | Bianco | 156/199 |
| 4,216,772 | 8/1980 | Tsuchiya et al. | 128/284 |
| 4,223,677 | 9/1980 | Anderson | 128/287 |
| 4,307,721 | 12/1981 | Tsuchiya et al. | 128/290 W |
| 4,360,022 | 11/1982 | Usami et al. | 128/290 R |
| 4,364,992 | 12/1982 | Ito et al. | 428/283 |
| 4,377,615 | 3/1983 | Suzuki et al. | 428/213 |
| 4,397,644 | 8/1983 | Matthews et al. | 604/378 |
| 4,405,326 | 9/1983 | Lenaghan | 604/385 |
| 4,480,000 | 10/1984 | Watanabe et al. | 428/284 |
| 4,554,191 | 11/1985 | Korpman | 428/35 |
| 4,578,066 | 3/1986 | O'Connor | 604/366 |
| 4,578,070 | 3/1986 | Holtman | 604/378 |
| 4,610,678 | 9/1986 | Weisman et al. | 604/368 |
| 4,673,402 | 6/1987 | Weisman et al. | 604/368 |
| 4,681,577 | 7/1987 | Stern et al. | 604/378 |
| 4,685,914 | 8/1987 | Holtman | 604/368 |
| 4,699,823 | 10/1987 | Kellenberger et al. | 428/219 |
| 4,753,644 | 6/1988 | Cottenden et al. | 604/378 |
| 4,794,034 | 12/1988 | Nishizawa et al. | 428/218 |
| 4,798,603 | 1/1989 | Meyer et al. | 604/378 |
| 4,908,026 | 3/1990 | Sukiennik et al. | 604/378 |
| 5,037,409 | 8/1991 | Chen et al. | 604/370 |

FOREIGN PATENT DOCUMENTS

| | | |
|---|---|---|
| 0140470 | 5/1985 | European Pat. Off. . |
| 126803 | 1/1990 | Taiwan, Prov. of China . |
| 138456 | 7/1990 | Taiwan, Prov. of China . |

Primary Examiner—Randall L. Green
Assistant Examiner—Rob Clarke
Attorney, Agent, or Firm—Thomas M. Gage; Thomas J. Mielke

[57] ABSTRACT

A feminine guard product capable of absorbing urine applied to said product in relatively small amounts at a relatively low velocity or in relatively large amounts at a relatively high velocity and menses. The feminine guard comprises an outer shell which defines a basin having a volume, an absorbent structure present in said basin, an acquisition layer comprising hydrophilic fibers and present in said basin, and a body side liner having a passage volume of 40 percent and being attached to the outer shell and covering the basin.

11 Claims, 2 Drawing Sheets

DISPOSABLE FEMININE GUARD

This is a continuation of application Ser. No. 07/598,272, filed on Oct. 16, 1990, now abandoned.

BACKGROUND OF THE INVENTION

1. Field of the Invention

The present invention relates to a disposable absorbent product. Specifically, the present invention relates to a feminine guard capable of absorbing both relatively high velocity/high quantity, and relatively low velocity/low quantity insults of urine and relatively low velocity/low quantity insults of menses.

2. Description of the Related Art

A relatively large number of women are, at some point in their life, faced with the problem of urinary incontinence. The severity of the incontinence varies from individual to individual over a wide range of possibilities. For example, some individuals are only slightly incontinent such that during periods of incontinence relatively small quantities, sometimes only a few drops, of urine are eliminated. Such small quantities of urine tend to be delivered with relatively little force at a relatively low velocity. Other individuals experience a more severe form of incontinence such that during periods of incontinence relatively large quantities of urine are eliminated with a relatively large force at a relatively high velocity. The problem of female incontinence can be further complicated during menstruation. Specifically, during periods of menstruation an absorbent protective device employed by the woman must be capable of absorbing not only urine but also menses.

A wide variety of absorbent products intended to absorb either urine or menses are available. Unfortunately, these products tend to be designed to absorb urine delivered under a certain set of conditions or menses. For example, U.S. Pat. No. 3,805,790 issued Apr. 23, 1974, to Kaczmarzyk, et al. is directed to a preshaped feminine napkin. The described feminine napkin has a predetermined shape dimensioned to conform well to the perineal area of a female body. The device may comprise a polymeric foam shell, which shell is filled with an absorbent such as cellulosic fibers and covered with a fluid-pervious cover. The device described by Kaczmarzyk et al. is designed and described as being particularly well suited for absorption of menstrual fluid.

U.S. Pat. No. 4,685,914 issued Aug. 11, 1987, to Holtman is directed to a disposable urinary pad. The described urinary pad comprises a liquid-impermeable, substantially flexible shell containing a fibrous web superstructure substantially filling the shell, and an absorbent medium between the superstructure and the bottom of the shell. The superstructure is formed from hydrophobic fibers. The device described by Holtman is designed primarily to absorb urine. Specifically, the device is believed suited to absorb relatively large discharges of urine delivered at a relatively high velocity. Due to the presence of the hydrophobic superstructure located between the body of a user and the absorbent medium, small quantities of urine delivered at a relatively low velocity are believed to remain on the upper surface of the hydrophobic surface of the superstructure. Since menses is similarly delivered at a relatively low velocity, the device described by Holtman is not believed to be well suited for absorption of menstrual fluid.

SUMMARY OF THE INVENTION

It is desirable to produce a disposable feminine guard which is capable of absorbing both urine and menses. The urine can be delivered to said feminine guard in relatively small quantities at a relatively low velocity (less than about 8 feet per second), or in relatively large quantities at a relatively high velocity (greater than about 11 feet per second). It is to this goal that the present invention is directed.

Disclosed is a feminine guard comprising a fluid-impervious, flexible outer shell, said shell defining a basin having a length, width, volume, and a rim. Present in the basin of the shell is a fibrous absorbent structure capable of absorbing and holding a discharged body fluid. The absorbent structure fills from about 10 to about 95 volume percent of the volume of the basin. Also present in the basin is an acquisition layer capable of rapidly absorbing and temporarily holding body fluids. The acquisition layer comprises a fibrous web of dry resilient fibers with at least about 30 weight percent of said fibers being hydrophilic. The acquisition layer fills from about 5 to about 50 volume percent of the basin. Covering the basin and attached to the rim is a fluid-pervious body side liner. The body side liner is structurally adapted to readily pass body fluids delivered at relatively low velocities. Specifically, the body side liner has a passage volume (as hereinafter defined) of 40 percent. The acquisition layer is adjacent the body side liner and is located between the liner and the absorbent structure. The acquisition layer and absorbent structure are specifically adapted and positioned such that the absorbent structure can desorb a liquid present in the acquisition layer.

DETAILED DESCRIPTION OF THE INVENTION

The present invention relates to a feminine guard capable of absorbing urine delivered in relatively small quantities at a relatively low velocity, urine delivered in relatively large quantities at a relatively high velocity, and menses. The ability to function in this manner results from the careful selection and arrangement of the components which comprise the described feminine guard.

Figure 1:
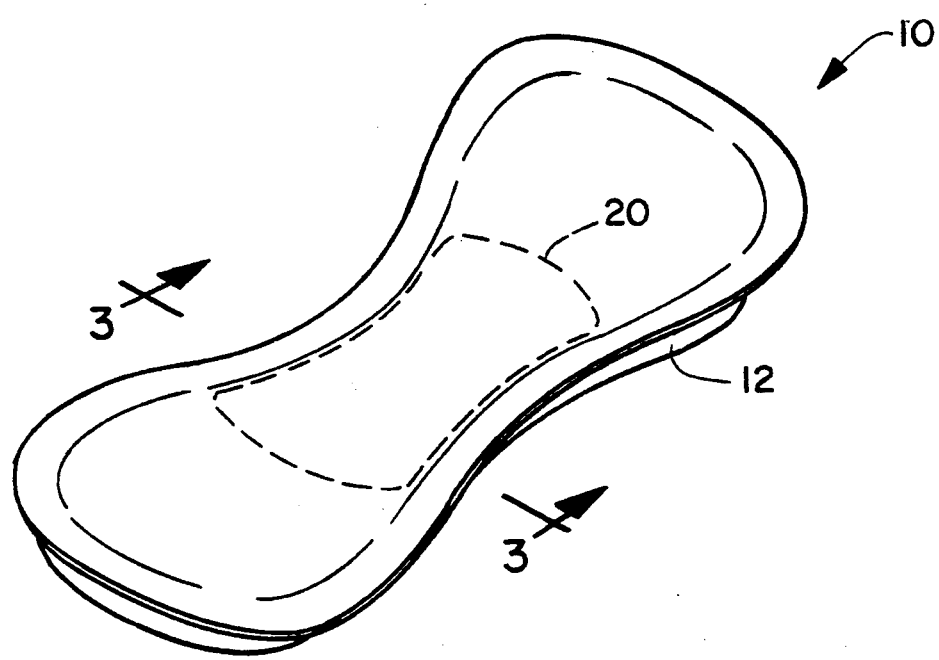
FIG. 1 is a perspective view of a feminine guard according to the present invention.
Figure 2:
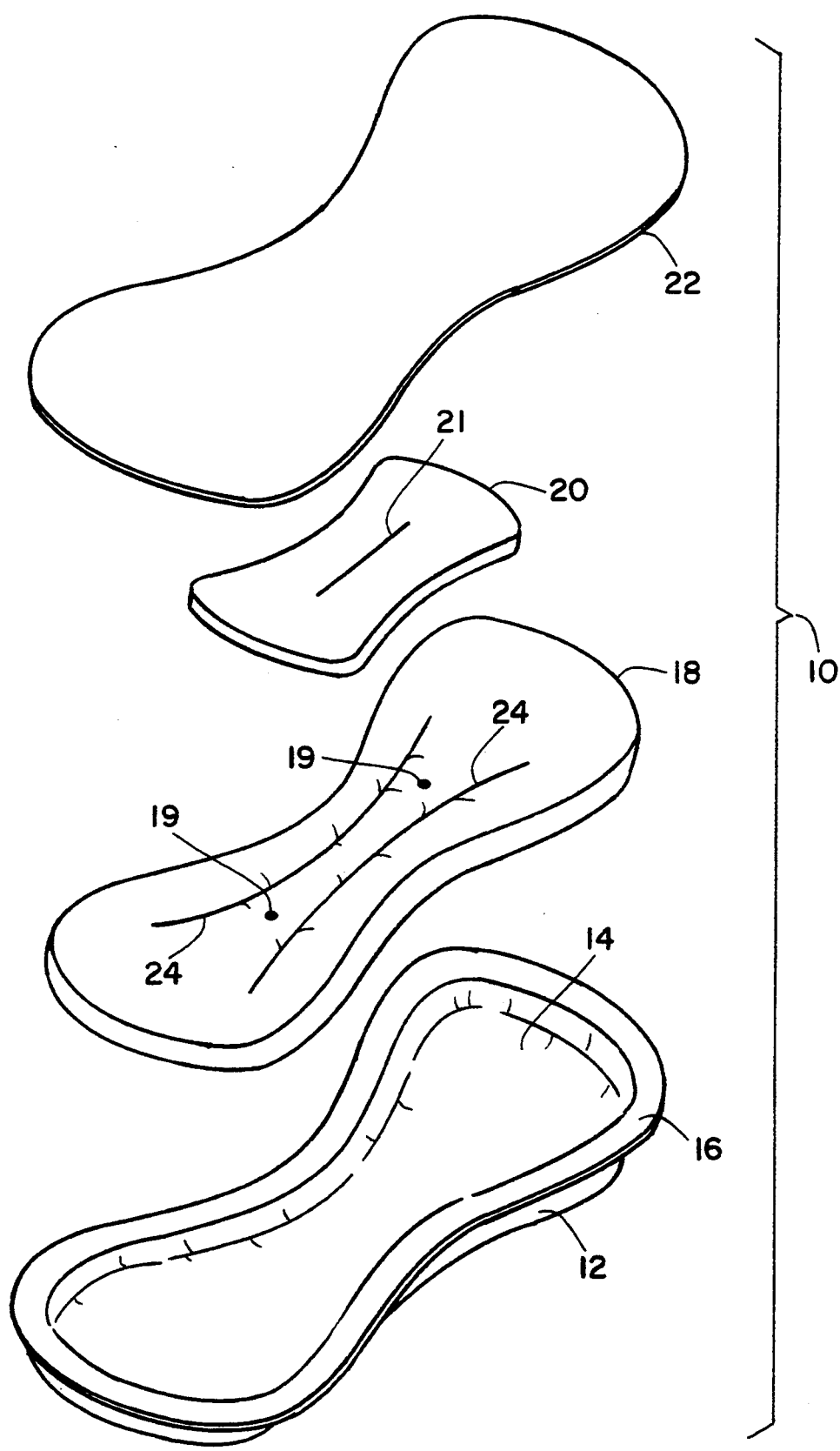
FIG. 2 is an exploded perspective view of the feminine guard of FIG. 1.

The feminine guard of the present invention can best be understood by reference to the drawings wherein FIG. I illustrates a perspective view of a preferred embodiment according to the present invention. FIG. 2 is an exploded perspective view of the feminine guard illustrated in FIG. 1. The feminine guard comprises four separate components. Specifically, the feminine guard 10 comprises an outer shell 12, which outer shell defines a basin 14 and a rim 16. The basin 14 has a length, width, and volume. Contained within the basin 14 is a fibrous absorbent structure 18. Superposed on top of the absorbent structure 18 is an acquisition layer 20. The acquisition layer 20 is also located within the basin 14 and sits on top of and in fluid communication with the absorbent structure 18. In the illustrated embodiment, dots of adhesive 19 secure acquisition layer 20 to absorbent structure 18. Finally, a body side liner 22 covers the basin 14 formed by the outer shell 12 with the body side liner being attached to the outer shell 12 along the periphery of the rim 16. Thus, the acquisition layer is located between said liner and said absorbent structure.

The components discussed above will now be described in more detail with various preferred embodiments of the present invention being discussed.

The outer shell 12 is formed from a fluid-impervious, flexible material. Exemplary of materials suitable for use in forming the outer shell 12 are various thermoplastic or thermosetting polymeric resins such as polyethylene, polypropylene, polyurethane, polyesters, and the like. In one preferred embodiment of the present invention, the outer shell 12 is formed from a thin layer of polyethylene foam commercially available from Voltek Inc. of Lawrence, Mass., under the trade designation Volara. Other thermoplastic or thermosetting polymeric foams are suitable for use in the present invention.

In one preferred embodiment, the outer shell 12 possesses sufficient structural rigidity to form a stand-alone, three-dimensional shell. In such a case, the outer shell suitably has a thickness of from about 0.01 inch to about 0.25 inch, preferably from about 0.03 inch to about 0.125 inch. However, it is also believed that the outer shell could be formed from a material lacking sufficient structural rigidity to form a stand-alone, three-dimensional shell but which, when filled with or attached to the other components of the feminine guard, takes on the illustrated configuration. Exemplary of such a material would be a polyethylene or polypropylene film having a thickness of about 0.001 inch. In any event, the outer shell is generally sufficiently flexible to readily conform to pressures exerted on it during use by a wearer.

The outer shell 12 can be formed from a variety of manufacturing processes such as thermoforming, vacuum forming, injection molding, mechanical forming, and the like.

For a desirable fit, the outer shell 12 suitably has a length of from about 4 to about 12 inches, a width of from about 1.3 to about 7 inches, and a depth of from about 0.25 to about 2.5 inches. In the illustrated embodiment, the outer shell 12 has a center section which is more narrow than the longitudinal end sections. The illustrated embodiment has been found to be particularly comfortable for a wearer during use. The difference in width between the center section and the longitudinal end sections of the feminine guard can vary. However, it is desired that a central section of the feminine guard have a width which is from about 10 to about 70 percent, and preferably from about 25 to about 50 percent less than the width of at least one of the longitudinal end sections of the feminine guard. In the illustrated embodiment, the feminine guard possesses the same width at each longitudinal end section. Moreover, the narrowest portion of the feminine guard is located generally in its center. Nonetheless, it is understood that the longitudinal end sections of the guard may have the same or different widths and that the narrowest portion of the feminine guard may be located in the longitudinal center of the feminine guard or may be offset towards either end of the feminine guard.

In one preferred embodiment, the feminine guard has a length of about 9.5 inches, a width at the longitudinal end sections of about 4.25 inches, and a width in the central section of about 2.88 inches. The outer shell 12 defines a basin 14 and a rim 16. The basin 14 has a length, a width, and volume. As can be seen from FIGS. 1 and 2, the length of the illustrated feminine guard comprises the length of the basin plus the width of the rim 16 at both longitudinal ends of the outer shell 12. The width of the illustrated feminine guard along any transverse line comprises the width of the basin plus the width of the rim on each longitudinal side of the outer shell. The width of the rim is suitably from about 0.06 to about 1.5 inches, preferably from about 0.25 to about 0.75 inch. It is generally preferred that the rim be continuous around the periphery of the basin 14 and have a generally uniform width. The depth of the feminine guard comprises the depth of the basin plus the thickness of the outer shell.

Present in the basin 14 is an absorbent structure 18. The absorbent structure is generally fibrous and is adapted to absorb and hold body fluids such as urine and menses. The absorbent structure 18 fills from about 10 to about 95 volume percent, preferably from about 50 to about 85 volume percent of the volume of the basin 14.

The absorbent structure 18 suitably has a thickness of from about 0.125 inch to about 1.5 inches, preferably from about 0.25 inch to about 1.0 inch. The absorbent structure 18 suitably comprises a pad of airlaid cellulosic fibers commonly referred to as wood pulp fluff. Conventional pads can have a density ranging from about 0.05–0.20 grams per cubic centimeter and are sufficiently flexible to readily conform to pressures exerted against the absorbent structure during use. The absorbent structure 18 may also comprise a pad of coform material composed of a mixture of cellulosic fibers and synthetic polymer fibers. For example, the coform material may comprise an airlaid blend of cellulosic fibers and meltblown polyolefin fibers such as polyethylene or polypropylene fibers. Additionally, it is possible for the absorbent structure 18 to be formed completely from meltblown polymeric fibers.

The absorbent structure 18 may also include an effective amount of an inorganic or organic high-absorbency material (also known as superabsorbent material) to enhance the absorptive capacity of the absorbent structure. For example, the absorbent structure can include from about 5 to about 95 weight percent of high-absorbency material and preferably includes from about 10 to about 30 weight percent of high-absorbency material to provide more efficient performance.

Suitable inorganic, high-absorbency materials include, for example, absorbent clays and silica gels. Organic high-absorbency materials can include natural materials such as agar, pectin, guar gum, and peat moss, as well as synthetic materials such as synthetic hydrogel polymers. Such hydrogel polymers include, for example, carboxymethylcellulose, alkali metal salts of polyacrylic acids, polyacrylamides, polyvinyl alcohol, ethylene maleic anhydride copolymers, polyvinyl ethers, hydroxypropylcellulose, polyvinyl morpholinone, polymers and copolymers of vinyl sulfonic acid, polyacrylates, polyacrylamides, polyvinyl pyridine, and the like. Other suitable polymers include hydrolyzed acrylonitrile grafted starch, acrylic acid grafted starch, and isobutylene maleic anhydride copolymers and mixtures thereof. The hydrogel polymers are preferably lightly crosslinked to render the material substantially water insoluble. Crosslinking may, for example, be by irradiation or by covalent, ionic, Van der Waals, or hydrogen bonding. Suitable materials are available from various commercial vendors, such as Dow Chemical Company, Celanese Corporation, Allied-Colloid Inc., and Stockhausen Inc. Typically the high-absorbency material is capable of absorbing at least about 15 times its weight in water, and preferably is capable of absorbing at least about 25–50 times its weight in water.

The high-absorbency material can be distributed or otherwise incorporated into the absorbent structure 18 employing various techniques. For example, the high-absorbency material can be substantially uniformly distributed in the mass of fibers comprising the absorbent structure. The high-absorbency material can also be non-uniformly distributed among the fibers to form, for example, a layer or a generally continuous gradient with either an increasing or decreasing concentration of superabsorbent material. In one preferred embodiment, the high-absorbency material forms an increasing gradient from that portion of the absorbent structure closest the body side liner to that portion farthest from the body side liner.

The absorbent structure 18 can optionally include a substantially hydrophilic tissue wrap 30 to help maintain the integrity of the fibrous structure.

The absorbent structure 18 is generally capable of desorbing the acquisition layer 20 to some degree. This aspect of the invention will be discussed in greater detail below.

Also present within the basin 14 is the acquisition layer 20. The acquisition layer 20 is structurally adapted to be able to rapidly absorb multiple insults of a relatively small amount of urine delivered at a relatively low velocity, multiple insults of a relatively large amount of urine delivered at a relatively high velocity, and menses. Specifically, the acquisition layer comprises a fibrous web of dry resilient fibers with at least about 30 weight percent of said fibers being hydrophilic. As used herein, a fiber will be considered to be hydrophilic when said fiber possesses a water-in-air contact angle of less than 90°, preferably of less than about 45°. The fibrous web of the acquisition layer comprises at least about 30 weight percent hydrophilic fibers. Beneficially, the fibrous web comprises at least about 50 weight percent, preferably at least about 90 weight percent hydrophilic fibers, and most preferably, about 95 weight percent hydrophilic fibers based on total weight of the fibrous web.

Those skilled in the art will recognize suitable hydrophilic fibers for forming the acquisition layer of the present invention. Exemplary of suitable fibers are inherently hydrophilic fibers such as rayon, cotton, and the like, as well as inherently hydrophobic fibers such as polyolefins and polyesters which have been rendered hydrophilic by surface treatment with a nonfugitive surface active agent. An inherently hydrophobic fiber will be considered to be hydrophilic when the fiber exhibits a water-in-air contact angle below 90°, preferably below about 45°, for three successive measurements with drying between each measurement.

When less than about 50 weight percent of the fibers of said fibrous web of the acquisition layers are hydrophilic, it is desirable that the hydrophilic fibers present in the acquisition layer be localized in discrete areas such that said discrete areas comprise at least 50 weight percent hydrophilic fibers based on total weight of such discrete areas. For example, clusters of hydrophilic fibers can be formed into a web of hydrophobic meltblown fibers such that the hydrophilic fibers form discrete areas comprising a majority of hydrophilic fibers.

Applicants have found that in order to get good absorption of small amounts of urine applied at a low velocity and menses, the acquisition layer should present areas that are hydrophilic. As a general rule, the more hydrophilic the acquisition layer is, the better the layer is able to absorb urine and menses.

The acquisition layer may comprise up to about 70 weight percent of hydrophobic fibers such as polyesters, polypropylene, polyethylene, and the like, and still perform in the desired manner. The acquisition layer temporarily holds the absorbed liquid and then releases the liquid to the absorbent structure. That is, the acquisition layer is desorbed by the absorbent structure. As a general rule, the absorbent structure is not able to absorb multiple insults of a liquid as rapidly as the acquisition layer and the acquisition layer is not able to hold as much liquid as the absorbent structure. By having both the absorbent structure and the acquisition layer present in the feminine guard, the guard is able to both rapidly absorb multiple insults of a liquid and to hold relatively large quantities of the liquid.

As used herein, a given fiber will be considered to possess dry resiliency when an acquisition layer, according to the present invention, formed from said fibers has a compression recovery value when dry of at least about 60 percent, preferably of at least about 80 percent.

The compression recovery value is a measure of the resilience of the material and is determined by measuring the original thickness of the acquisition layer under a restraining pressure of 0.068 pounds per square inch (0.47 kPa). The acquisition layer is then subjected to a compression force of 0.5 pounds per square inch (3.45 kPa) for 60 seconds. This compression force is then removed and, after four minutes, the recovery thickness of the material is measured under the original pressure of 0.068 psi (0.47 kPa). The compression recovery value is then determined by dividing the recovery thickness by the original thickness and is reported as percent recovery.

In order to enable the acquisition layer to perform as described, the acquisition layer desirably possesses certain physical characteristics in addition to being formed from dry resilient fibers of which at least about 30 weight percent are hydrophilic fibers. Specifically, the acquisition layer suitably has a thickness of from about 0.1 inch to about 1.0 inch, preferably of from about 0.1 inch to about 0.5 inch, most preferably of from about 0.15 inch to about 0.3 inch, and a basis weight of from about 40 to about 250 grams per square meter, preferably of from about 80 to about 130 grams per square meter. Additionally, the acquisition layer has a pore size which allows the acquisition layer to rapidly receive a liquid applied thereto in large quantities at a relatively high velocity and release the liquid to the absorbent structure.

The acquisition layer is present within the basin 14 and sits atop the absorbent structure 18. The acquisition layer suitably fills from about 5 to about 50, preferably from about 5 to about 30 volume percent of the basin. In one preferred embodiment, the acquisition layer is adhesively attached to the absorbent structure by dots or lines of hot melt, pressure sensitive, or other types of adhesives.

In one preferred embodiment of the present invention, the acquisition layer is formed from rayon fibers having an average fiber fineness of from about 2 denier to about 15 denier, preferably of from about 5.5 denier to about 8.0 denier. The web is formed by airlaying the fibers and then needling the air laid web. The web has a latex binder comprising vinyl acetate applied thereto to adhere certain fiber-fiber intersections together. Exemplary of such a material is a rayon web, commercially available from Sackner Products Inc., Grand Rapids, Mich., under the trade designation SN-92.

In the preferred embodiment of the present invention wherein the acquisition layer is formed from rayon fibers, the acquisition layer has a thickness of about 0.25 inch and a basis weight of about 120 grams per square meter.

The acquisition layer can extend along the entire length and width of the basin. However, in the preferred embodiment the acquisition layer has a length which is less than the length of the basin and a width which is substantially the same as the width of the basin. Most preferably, the acquisition layer is located only in the central $\frac{1}{3}$ to $\frac{2}{3}$ of the length of the basin 14. Applicants have discovered that when the acquisition layer is located only in the central $\frac{1}{3}$ to $\frac{2}{3}$ of the length of the basin, liquid applied to the acquisition layer can transfer through the length of the acquisition layer, out the ends of the acquisition layer and be absorbed by the absorbent structure at portions of the absorbent structure remote from that area most likely to receive additional insults of a liquid. By having the length of the acquisition layer be $\frac{1}{3}$ to $\frac{2}{3}$ of the length of the basin, the likelihood of leakage due to liquid transfer to the end edges of the basin is lessened. In one preferred embodiment, the acquisition layer is embossed along at least a portion of its length. This embossed line is illustrated in FIG. 2 and is designated by reference numeral 21. The embossed line has been found to encourage the acquisition layer to flex towards the absorbent structure when a transverse force is applied to the feminine guard. This, in combination with adhesive dots 19, assists with maintaining the acquisition layer in fluid communication with the absorbent structure which results in improved fluid transfer efficiency between the acquisition layer and the absorbent structure.

The acquisition layer is in fluid communication with the absorbent structure such that a liquid present in the acquisition layer is drawn from the acquisition layer into the absorbent structure. To accomplish this, there must be a capillary pressure gradient between the acquisition layer and the absorbent structure, such that a liquid present in the acquisition layer is drawn from the pores of the acquisition layer into the pores of the absorbent structure. Those skilled in the art will recognize that a number of variables influence the capillary pressure including the surface tension of a liquid, the liquid-fiber contact angle and the capillary radius. Those skilled in the art can adjust the liquid-fiber contact angle and capillary radius in order to ensure the required degree of transfer between the acquisition layer and the absorbent structure. In this manner, the absorbent structure can desorb the acquisition layer to prepare the acquisition layer to receive subsequent insults of a liquid and to provide the surface of the feminine guard in contact with the user with a relatively dry feel.

A body side liner 22 covers the top of the basin 14 and is attached to the outer shell 12 along the rim 16. The body side liner is typically composed of a liquid-permeable, substantially hydrophobic, fibrous material such as spunbonded web composed of synthetic polymer filaments. Alternatively, body side liner 22 may comprise a meltblown web or a bonded-carded web composed of synthetic polymer filaments. Suitable synthetic polymers include, for example, polyethylene, polypropylene, polyesters, and combinations thereof. The body side liner suitably has a basis weight of from about 10 to about 30 grams per square meter, and preferably of from about 12 to about 20 grams per square meter. An apertured film may also be employed as the body side liner.

Applicants have found that it is generally desirable to have the body side liner formed from a hydrophobic material to increase the skin dryness of the feminine guard. Unfortunately, such hydrophobic materials can cause a liquid applied thereto at a low velocity to remain on top of the liner and not pass into the acquisition layer. This often causes the product to leak.

Body side liners suitable for use in the present invention possess a passage volume of 40 volume percent. As used herein, passage volume refers to the volume percent of a drop of distilled water which passes through the liner when applied at a velocity of 6.5 feet per second. The method by which passage volume is determined is set forth in greater detail below.

Applicants have found that body side liners having a passage volume of 40 volume percent are able to pass urine applied in relatively small amounts at low velocity and menses into the acquisition layer. Body side liners not able to meet this standard tend to cause urine applied in small amounts at a low velocity and menses to pool on their surface and run off. Preferably, the body side liners of the present invention have a passage volume of 40 volume percent and most preferably of 60 volume percent. Body side liners may be treated with a surface active agent to increase their passage volume.

In one preferred embodiment, body side liners with relatively high passage volumes (greater than about 50 volume percent) are employed with acquisition layers comprising a relatively low concentration of hydrophilic fibers while body side liners with relatively low passage volumes (less than about 50 volume percent) are employed with acquisition layers comprising a relatively high concentration of hydrophilic fibers.

In one preferred embodiment, the body side liner is a bonded carded web containing 50 weight percent 3 denier polypropylene fibers and 50 weight percent of a polyethylene sheath polypropylene core fiber (50 weight percent polyethylene, 50 weight percent polypropylene). The polypropylene fibers are formed into a carded web having a basis weight of 8 grams per square meter. The sheath/core fibers are also formed into an 8 gram per square meter carded web. The two carded webs are placed one on top of another and through air bonded. Such a body side liner is commercially available from Chori America Inc., Los Angeles, Calif., under the trade designation NBF(H).

The body side liner can be attached to the feminine guard at rim 16 in a variety of manners known to those skilled in the art. For example, the body side liner may be adhesively bonded to the rib or may be thermally or ultrasonically bonded.

As discussed above, the acquisition layer and body side liner are specifically designed to receive and pass urine applied to the feminine guard either in relatively small volumes at a low velocity, or in relatively large volumes at a relatively high velocity.

Applicants have discovered that by using a body side liner having a passage volume of 40 volume percent, and by forming the acquisition layer from a hydrophilic material, the acquisition layer can absorb urine applied at a relatively high velocity, but can also absorb urine and menses which are applied at a relatively low velocity.

Figure 3:
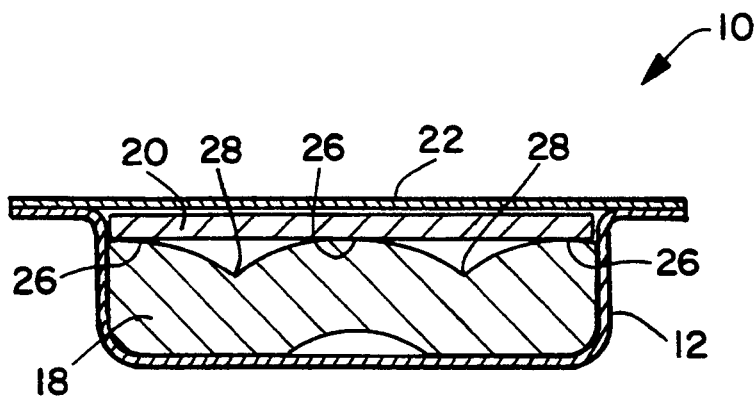
FIG. 3 is a cross section taken along line 3—3 of FIG. 1.

In the preferred embodiment illustrated in the figures, the absorbent structure 18 has a generally rectangular shape having a length of 8.5 inches and a width of 3.5 inches. The length of the absorbent structure 18 is substantially the same as the length of the basin. Since the outer shell 12 and basin 14 are not generally rectangular in shape, it is necessary to "pinch" the center of absorbent structure 18 in order to place it into the basin 14. To aid in this process, 2 parallel lines 24 approximately 4 inches in length are embossed generally centrally on the absorbent structure 18. The presence of the embossed lines 24 assists in the absorbent structure 18 in forming a W-fold when pinched in the center area. This W-fold can best be seen from reference to FIG. 3 where it is seen that the top surface of the absorbent structure 18 tends to form the shape of an elongated W. The presence of the W-fold in the center of the feminine guard brings several advantages.

Specifically, the W-fold allows contact between the absorbent structure 18 and the acquisition layer 20 at points of contact 26. This allows fluid transfer from the acquisition layer into the absorbent structure. Additionally, the W-fold produces channels 28 which allow liquid applied to the feminine guard in large quantities at a high velocity to pass through the body side liner and acquisition layer into the channels 28 and flow along the length of the absorbent structure until sufficient time has elapsed to allow the liquid to be absorbed by the absorbent structure 18 which, as discussed above, is generally slower to absorb a liquid than the acquisition layer.

In use, the feminine guard is positioned between a wearer's legs in a manner similar to a feminine napkin. The feminine guard may be maintained in position due to pressure exerted by the wearer's underclothes or may be attached to the wearer's underclothes with any of a variety of attachment means known to those skilled in the art. For example, the feminine guard may be attached to the underclothes of a wearer throught the use of an adhesive strip applied to the outer surface of the outer shell.

The feminine guard is, during use, subjected to transverse compression caused by the legs of a wearer. The degree of transverse compression varies during the time the product is in use. It is generally desirable, to prevent leakage, that the feminine guard be able to recover from transverse compression to regain its shape prior to compression. One way of measuring the ability of the feminine guard to regain its original shape after transverse compression is to measure the transverse compression recovery of the feminine guard. The transverse compression recovery is determined by measuring the width of the feminine guard. The feminine guard is then subjected to a compressive force which reduces the overall width by 75 percent of the original width. The compressive force is released and four minutes are allowed to pass. The width of the feminine guard is then determined. The transverse compression recovery is calculated by dividing the recovery width by the original width and is reported as percent recovery. As a general rule, it is desired that the feminine guard described above have a transverse compression recovery of at least about 80 percent.

TEST METHODS

Passage Volume

A 6 inch by 4 inch sample of the liner material to be tested is provided. The liner is placed on top of a tared beaker. A burette is provided containing an aqueous solution containing 0.9 weight percent of sodium chloride. The tip of the burette is placed 8 inches above the surface of a liner as it sits on top the tared beaker. Five drops (about 0.042 grams per drop) are allowed to fall from the burette onto the liner to be tested. The liner is shifted between application of each drop so that a new, dry, contact point for the drop on the liner is presented. The beaker is then reweighed and the weight of saline solution present in the beaker determined. The weight of 5 drops of saline solution is determined by allowing 5 drops to fall into the beaker without the presence of a liner material. The velocity at which the drop strikes the liner is calculated by the formula $V_f = (2\ gh)^{\frac{1}{2}}$ wherein $V_f$ is the final velocity, g is the acceleration due to gravity and h is the height. When h equals 8 inches (0.67 feet), $V_f [2(32)(0.67)]^{\frac{1}{2}} = 6.5$ feet per second. Those skilled in the art will recognize that, given the velocity and weight of the drop, one can calculate the force or pressure with which the drop strikes the surface of the liner (assuming a constant velocity). The passage volume is then determined by dividing the weight of a liquid passing through the liner by the weight of 5 drops of liquid. Since volume is directly proportional to weight under these circumstances, the percent passage based on weight is directly related to the percent passage based on volume and is referred to as passage volume for ease of understanding.

EXAMPLE

A number of materials believed suitable for use as liners on absorbent products are tested to determine the passage volume of the liner material. Unless otherwise stated, all of the liners are bonded carded webs formed from staple fibers less than three inches in length. All of the webs are formed to have a basis weight of about 16 grams per square meter. The fibers are of various denier and are bonded through one of two methods. The webs are either point bonded so that either 15 percent or 30 percent of the total area of the liner is subjected to an elevated temperature and pressure whereby the fibers are melt fused together, or the webs are through-air bonded whereby hot air is passed through the carded webs such that the fibers soften and, thereby, adhere to one another at their points of intersection. Those skilled in the art are familiar with methods for point bonding and through-air bonding of carded webs. The materials from which the individual webs are formed are described below in connection with each of the webs tested. The following webs are employed:

Sample No. 1—A bonded carded web formed from 2 denier bi-component fibers which fibers comprise 50 weight percent polypropylene and 50 weight percent polyethylene in a sheath/core configuration wherein the polyethylene forms the sheath. The web is point bonded over 15 percent of its total surface area.

Sample No. 2—A bonded carded web formed from the fibers of Sample No. 1 wherein the web is point bonded over 30 percent of its total surface area.

Sample No. 3—A bonded carded web formed from the fibers of Sample No. 1 wherein the web is through-air bonded.

Sample No. 4—A bonded carded web formed from 50 weight percent of a 2 denier bi-component polypropylene polyethylene core/sheath fiber (50/50, polyethylene sheath) and 50 weight percent of a 0.5 denier polypropylene fiber. The web is point bonded over 30 percent of its total surface area.

Sample No. 5—A bonded carded web formed from the fibers of Sample No. 4 except the polypropylene fibers have a denier of 3.0. The web is point bonded over 30 percent of its total surface area.

Sample No. 6— A bonded carded web formed from 2 denier bi-component core/sheath fibers formed from 50 weight percent polypropylene and 50 weight percent polyethylene wherein the polyethylene forms the sheath. The web is point bonded over 15 percent of its total surface area.

Sample No. 7—A bonded carded web formed from the fibers of Sample No. 5 except the polypropylene/polyethylene sheath-core fibers comprise 50 weight percent of fibers having a denier of 2 and 50 weight percent of fibers have a denier of 3. The web is point bonded over 15 percent of its total surface area.

Sample No. 8—A bonded carded web formed from the fibers of Sample No. 4 wherein the web is through-air bonded.

Sample No. 9—A bonded carded web formed from the fibers of Sample No. 6 wherein the web is through-air bonded.

Sample No. 10—A bonded carded web formed from the fibers of Sample No. 7 wherein the web is through-air bonded.

Sample No. 11—A bonded carded web formed from 2 denier bi-component sheath/core fibers comprising 50 weight percent polyethylene (sheath) and 50 weight percent polyethyleneterephthalate (core). The carded web is through-air bonded.

Sample No. 12—A bonded carded web formed from the fibers of Sample No. 11 wherein the web is point bonded over 15 percent of its total surface area.

Sample No. 13—A bonded carded web formed from the fibers of Sample No. 11 wherein the web is point bonded over 30 percent of its total surface area.

Sample No. 14—A bonded carded web formed from 2 denier bi-component fibers comprising 50 weight percent polyethylene and 50 weight percent polyethyleneterephthalate in a sheath/core arrangement. The polyethylene forms the sheath of the bi-component fiber. The web is point bonded over 30 percent of its total surface area.

Sample No. 15—A bonded carded web formed from the fibers of Sample No. 14 wherein the web is through-air bonded.

Sample No. 16—A bonded carded web formed from 1.8 denier bicomponent fibers. The bicomponent fibers are in a sheath/core configuration and comprise 50 weight percent polyethylene as the sheath and 50 weight percent polyethyleneterephthalate as the core. The web is through-air bonded.

Sample No. 17—A bonded carded web formed from the fibers of Sample No. 16 wherein the web is point bonded over 30 weight percent of its total surface area.

Sample No. 18—A bonded carded web prepared from the fibers of Sample No. 16 wherein the web is point bonded over 15 percent of its total surface area.

Sample No. 19—A bonded carded web comprising 50 weight percent of the bicomponent fibers of Sample No. 16 and 50 weight percent of 0.5 denier polypropylene fibers. The carded web is point bonded over 30 percent of its total surface area.

Sample No. 20—A bonded carded web formed from the fibers of Sample No. 19 except that the carded web is through-air bonded.

Sample No. 21—A two-layered bonded carded web. The first layer comprises 2 denier bicomponent fibers. The bicomponent fibers comprise 50 weight percent polyethylene and 50 weight percent polypropylene in a sheath/core configuration. The polyethylene forms the sheath of the bicomponent fiber. The second layer comprises 3 denier polypropylene fibers. Carded webs having a basis weight of about 8 grams per square meter are formed from the bicomponent fibers and the polypropylene fibers. The two 8 gram per square meter webs are then placed one on top of another and through-air bonded.

Sample No. 22—A 16 gram per square meter spunbonded web is formed from polypropylene fibers having a denier of about three. The spunbonded web is treated with about 0.1 weight percent of an ionic surfactant commercially available from The Rohm & Haas Company under the trade designation Triton X-102.

The materials described above are then subjected to the passage volume testing as set forth above. The results of this testing are set forth in Table 1.

TABLE 1

| Sample No. | Passage Volume |
| --- | --- |
| 1 | 6 |
| 2 | 18 |
| 3 | 20 |
| 4 | 10 |
| 5 | 54.5 |
| 6 | 17 |
| 7 | 29 |
| 8 | 15 |
| 9 | 30 |
| 10 | 31 |
| 11 | 67 |
| 12 | 69 |
| 13 | 40 |
| 14 | 51 |
| 15 | 66 |
| 16 | 37 |
| 17 | 65.5 |
| 18 | 39 |
| 19 | 3.0 |
| 20 | 4.5 |
| 21 | 44 |
| 22 | 21 |

As can be seen from reference to Table 1, many materials which would appear to be suitable for use as liners in absorbent products, are not suitable for use in the product according to the present invention because the liners do not possess a sufficiently high passage volume.

While the present invention has been described in particular reference to a preferred embodiment, the present invention is susceptible of being embodied with various alterations and modifications which may differ particularly from those that have been described in the preceding specification. These variations and alterations are possible without departing from the scope of the invention.

What is claimed is:

1. An absorbent product, said product comprising:
  (a.) a fluid-impervious, flexible outer shell having a length of from about 4 to about 12 inches, a width of from about 1.3 to about 7 inches, and a depth of from about 0.25 to about 2.5 inches, said shell defining a basin having a length, width, volume, and a rim;

(b) a fluid-pervious body side liner attached to said shell at said rim, said liner having a passage volume of 40 percent;

(c) a fibrous absorbent structure present in said shell and filling from about 10 to about 95 volume percent of said volume of said basin;

(d) an acquisition layer present in said basin and located between said liner and said absorbent structure, said acquisition layer comprising a fibrous web of dry resilient fibers, at least about 30 weight percent of said fibers possessing a water-in-air contact angle of less than about 45 degrees, said acquisition layer filling from about 5 to about 50 volume percent of said volume of said basin; and wherein said acquisition layer can be desorbed by said absorbent structure and said fibers of said acquisition layer are rayon fibers.

2. The absorbent product according to claim 1 wherein said rayon fibers have a fiber fineness of from about 2 denier to about 15 denier.

3. The absorbent product according to claim 2 wherein said rayon fibers are bonded together at certain fiber-fiber intersections.

4. An absorbent product, said product comprising:

(a) a fluid-impervious, flexible polymeric foam outer shell having a length of from about 4 to about 12 inches, a width of from about 1.3 to about 7 inches, and a depth of from about 0.25 to about 2.5 inches, said shell defining a basin having a length, width, volume, and a rim;

(b) a fluid-pervious body side liner attached to said shell at said rim, said liner having a passage volume of 40 percent;

(c) a fibrous absorbent structure present in said shell and filling from about 10 to about 95 volume percent of said volume of said basin;

(d) an acquisition layer present in said basin and located between and in fluid communication with said liner and said absorbent structure, said acquisition layer comprising a fibrous web of dry resilient rayon fibers possessing a water-in-air contact angle of less than about 45 degrees, said rayon fibers being bonded together at certain fiber-fiber intersections and having a fineness of from about 2 denier to about 15 denier, and filling from about 5 to about 30 volume percent of said volume of said basin; and wherein said acquisition layer can be desorbed by said absorbent structure.

5. The absorbent product according to claim 4 wherein said body side liner comprises a bonded carded web having a passage volume of 60 percent.

6. The absorbent product according to claim 4 wherein the width of said basin is less in the center than at opposite longitudinal ends.

7. The absorbent product according to claim 4 wherein said absorbent structure comprises a web of hydrophilic fiber material and a high-absorbency material.

8. The absorbent product according to claim 7 wherein said absorbent structure comprises an airlaid mixture of wood pulp fluff and a high-absorbency material, said absorbent structure being embossed along two generally parallel longitudinal lines whereby said absorbent structure can be W-folded.

9. The absorbent product according to claim 8 wherein said absorbent structure has a length which is substantially the same as the length of said basin, and a width which is greater than the width of the center of said basin.

10. The absorbent product according to claim 4 wherein the length of said acquisition layer is between about ⅓ and about ⅔ of the length of said basin.

11. The absorbent structure according to claim 10 wherein said absorbent product has a transverse compression recovery of at least about 80 percent.

* * * * *